(12) United States Patent
Zingde et al.

(10) Patent No.: US 8,492,100 B2
(45) Date of Patent: Jul. 23, 2013

(54) AUTOANTIBODIES FOR PROTEIN ANTIGENS AS MARKERS FOR CANCER OF GINGIVO-BUCCAL COMPLEX

(75) Inventors: Surekha Mahesh Zingde, Navi Mumbai (IN); Sanjeev Shukla, Navi Mumbai (IN); Ravi Sirdeshmukh, Hyderabad (IN); Curam Sreenivasacharlu Sundaram, Hyderabad (IN); Anil Keith D'Cruz, Maharashtra (IN); Kumar Alok Pathak, Mumbai (IN); Shubhada Vijay Kane, Mumbai (IN)

(73) Assignee: Council of Scientific and Industrial Research, New Delhi (IN)

( * ) Notice: Subject to any disclaimer, the term of this patent is extended or adjusted under 35 U.S.C. 154(b) by 334 days.

(21) Appl. No.: 12/527,271

(22) PCT Filed: Feb. 7, 2008

(86) PCT No.: PCT/IN2008/000076
§ 371 (c)(1),
(2), (4) Date: Apr. 11, 2011

(87) PCT Pub. No.: WO2008/099419
PCT Pub. Date: Aug. 21, 2008

(65) Prior Publication Data
US 2011/0189699 A1 Aug. 4, 2011

(30) Foreign Application Priority Data
Feb. 14, 2007 (IN) .............................. 290/DEL/2007

(51) Int. Cl.
*A61K 35/12* (2006.01)
*G01N 33/53* (2006.01)

(52) U.S. Cl.
USPC ........... 435/7.1; 435/7.23; 436/64; 424/277.1

(58) Field of Classification Search
None
See application file for complete search history.

(56) References Cited

FOREIGN PATENT DOCUMENTS
WO 2006/073254 A1 7/2006

OTHER PUBLICATIONS

Ralhan, Clin Can Res 4:2147-52, 1998.*
Castelli et al Anticancer Res 21:753-8, 2001, IDS filed Sep. 15, 2010, item AL.*
Rye et al, J Hlsto & Cyto 32: 1145, 1984.*
Hospital Based Cancer Registry, Annual Report 2001, Department of Medical Records, Biostatistics & Epidemiology, Tata Memorial Hospital, Mumbai, 2005.
Castelli, M., et al., Anti-p53 and Anti-Heat shock Proteins antibodies in Patients with Malignant or Pre-malignant Lesions of the Oral Cavity, *Anticancer Research*, vol. 21, No. 18, Jan. 2001, pp. 753-758.
Kaur, J., et al., "Serum p53 antibodies in patients with oral lesions: correlation with p53/HSP70 complexes", *International Journal of Cancer*, vol. 74, No. 6, Dec. 19, 1997, pp. 609-613.
Fuji, A., et al., "Autoantibodies against the amino terminal of alpha-enolase are a useful diagnostic marker of Hashimoto's encephalopahy", *Journal of Neuroimmunology*, vol. 162, No. 1-2, May 2005, pp. 1-2.
Ping, H., et al., "Proteomics-based identification of α-enolase as a tumor antigen in non-small lung cancer", *Cancer Science* vol. 98, No. 8, Aug. 2007, pp. 1234-1240.
Shukla, S, et al., "Tumor antigens eliciting autoantibody response in cancer of gingivo-buccal complex" *Proteomics Clinical Applications*, vol. 1, No. 12, Dec. 2007, pp. 1592-1604.

* cited by examiner

*Primary Examiner* — Lei Yao
(74) *Attorney, Agent, or Firm* — Ladas & Parry LLP

(57) ABSTRACT

The present invention relates to identification of a set of proteins, which elicit an autoantibody response in patients with cancer of gingivo-buccal complex. Systematic comparisons of serum samples from clinically normal individuals and from patients with cancer of gingivo-buccal complex has revealed significant differences in the presence of autoantibodies in sera against cellular antigens present in a cancer cell line. The autoantibody response to a single or combination of these protein antigens serves as a novel marker and can be utilized for screening, early detection, prognosis, and potential target for therapy. The invention also provides for the use of the identified protein antigens in immunoassays designed to detect the presence of serum antibodies to the specific protein antigens in sera from individuals that harbor such antibodies. The invention also relates to the use of the identified antigens as immunogens for stimulation of an immune response in patients expressing such protein antigens. The invention is demonstrated by way of example in which elevated levels of circulating antibodies reactive against tumor specific antigens were identified in sera derived from patients with cancer of gingivo-buccal complex. The utility of identified antigens for early detection is assessed by analysis of sera from patients with leukoplakia of gingivo-buccal complex.

10 Claims, 2 Drawing Sheets

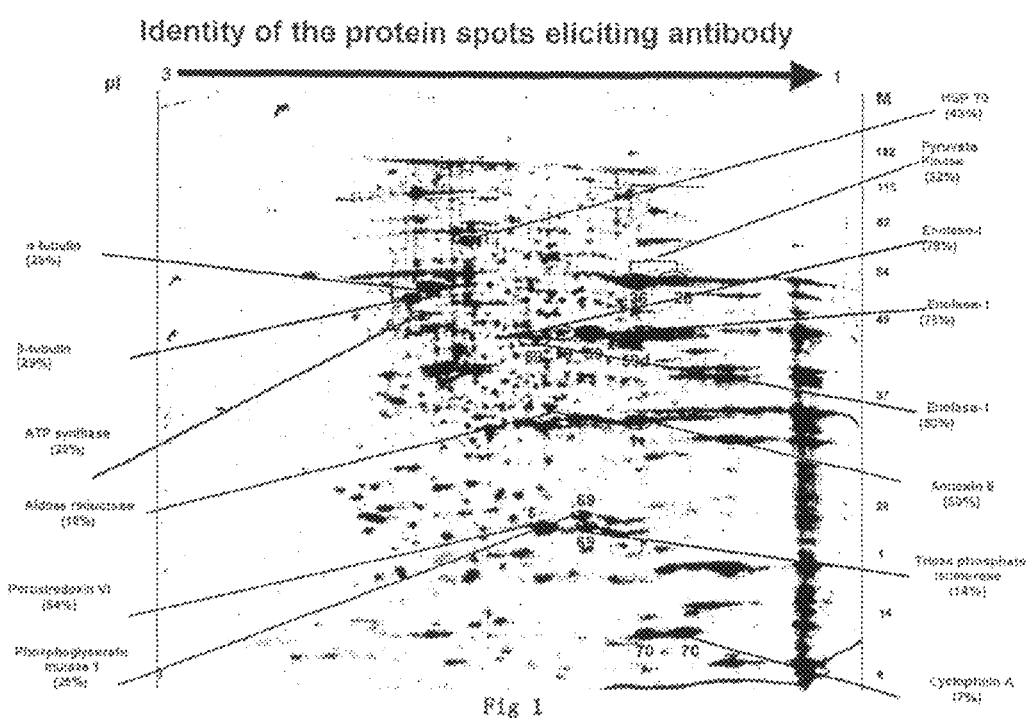

AUTOANTIBODIES FOR PROTEIN ANTIGENS AS MARKERS FOR CANCER OF GINGIVO-BUCCAL COMPLEX

FIELD OF INVENTION

The present invention relates to identification of a set of proteins, which elicit an autoantibody response in patients with cancer of gingivo-buccal complex. Systematic comparisons of serum samples from clinically normal individuals and from patients with cancer of gingivo-buccal complex has revealed significant differences in the presence of autoantibodies against several antigens present in an oral cancer cell line. The autoantibody response to a single or combination of these tumor antigens serves as novel marker and can be utilized for early detection, prognosis, and potential target for therapy. The invention also provides for the use of the identified protein antigens in immunoassays designed to detect the presence of serum antibodies to the specific protein antigens in sera from individuals that harbor such antibodies. The invention also relates to the use of the identified antigens as immunogens for stimulation of an immune response in patients expressing such protein antigens. The invention is demonstrated by way of example in which elevated levels of circulating antibodies reactive against tumor specific antigens were identified in sera derived from a patient with cancer of gingivo-buccal complex. The utility of the antigens identified for early detection has been assessed by analysis of sera of patients with leukoplakia of gingivo-buccal complex.

BACKGROUND OF THE INVENTION AND PRIOR ART

Oral cancer is the sixth common malignancy and is a major cause of cancer morbidity and mortality worldwide. Globally about 500,000 new oral and pharyngeal cancers are diagnosed annually, and three quarters of these are from the developing world (Gupta P C. 1982 "Comparison of carcinogenecity of betal quid with and without tobacco: an epidemiologic review." *Ecology of Disease* 1: 213-219; Saranath. 2000 "Integrated Biology and Molecular pathology of oral cancer. Contemporary issue in oral cancer." *Oxford university press:* 30-71). In India, at the Tata Memorial Hospital (Dinshaw and Ganesh. 2005 *Hospital Based Cancer Registry, Annual report* 2001, *Tata Memorial Hospital.*) cancers of the head and neck comprise of ~25% of cancers presenting in male with cancers of the oral cavity constituting ~12% of the total cancer load and 52% of the head and neck cases. Of these, cancers of the gingivo-buccal complex and those of the tongue are ~59% and ~21% respectively of the oral cavity. Most of the gingivo-buccal complex cancers present at stage III and IV.

At present the major modality for treatment of these cancers is surgery for stage III and IV cancers, followed by radiotherapy. Early stage cancers are often treated with surgery or radiotherapy alone. The five-year survival is very low and about 60% return with a recurrence or local nodal metastasis.

Major problem is that the choice of therapy for each patient is based on interpretation of clinical and histopathological observations in light of previous clinical experience. However, disease that is clinically similar can behave differently due to diverse combinations of molecular alterations determining disease prognosis. Use of molecular markers to help in prognostication of oral cancer is thus necessary.

Autoantibodies to qualitatively or quantitatively modified cellular proteins are known to be produced by patients in certain diseases such as autoimmune diseases and cardiovascular-related disorders, in some cases even before the onset of the disease. There is increasing evidence for an immune response to cancer in humans, as demonstrated in part by the identification of auto antibodies against a number of intracellular and surface antigens detectable in sera from patients with different cancer types (Le Naour. 2001 "contribution of proteomics to tumor immunology." *Proteomics* 1: 1295-302; Hanash. 2003 "Harnessing immunity for cancer marker discovery." *Nat Biotechnol* 21: 37-8; Yang and Yang. 2005 "New concepts in tumor antigens: Their significance in future immunotherapies for tumors." *Cellular and Molecular Immunology* 2: 331-341; Anderson and LaBaer. 2005 "The sentinel within: exploiting the immune system for cancer biomarkers." *J Proteome Res* 4: 1123-33). The detection of autoantibodies to cellular antigens and the identification of proteins that have elicited autoantibodies have been accomplished using a variety of approaches. Early studies involving the immune system investigated the circulating immune complexes to identify antigen-antibody complexes in circulation (Carpentier et al. 1982 "Circulating immune complexes and the prognosis of acute myeloid leukemia." *N Engl J Med* 307: 1174-80.) This was followed by SEREX analysis wherein a cDNA expression library from tumor tissue is screened with autologous/heterologous sera (Sahin et al. 1995 "Human neoplasms elicit multiple specific immune responses in the autologous host." *Proc Natl Acad Sci USA* 92: 11810-3; Old and Chen. 1998 "New paths in human cancer serology." *J Exp Med* 187: 1163-7). A recent modified approach involves the screening of a random peptide library with patient's sera (Mintz et al. 2003 "Fingerprinting the circulating repertoire of antibodies from cancer patients." *Nat Biotechnol* 21: 57-63). Several studies have identified autoimmunity against single different proteins such as p53, hsp 90, c-erbB-2/HER2/neu and mucin-related antigens in breast cancer (Lenner et al. 1999 "Serum antibodies against p53 in relation to cancer risk and prognosis in breast cancer: a population-based epidemiological study." *Br J Cancer* 79: 927-32; Conroy et al. 1998 "Autoantibodies to the 90 kDa heat shock protein and poor survival in breast cancer patients." *Eur J Cancer* 34: 942-3; Disis et al. 1997. "High-titer HER-2/neu protein-specific antibody can be detected in patients with early stage breast cancer." *J Clin Oncol* 15: 3363-3367; von Mensdorff-Pouilly et al. 1996 "Humoral immune response to polymorphic epithelial mucin (MUC-1) in patients with benign and malignant breast tumours." *Eur J Cancer* 32A: 1325-31). These studies have shown the presence of autoantibodies in variable amounts ranging from 10%-20% suggesting that several different factors that contribute to humoral response in individuals. A related study which has addressed the presence of p53 antigen and its antibody in different cancers (Soussi. 2000 "p53 Antibodies in the sera of patients with various types of cancer: a review." *Cancer Res* 60: 1777-88). and also in head and neck tumors (Soussi. 2000 "p53 Antibodies in the sera of patients with various types of cancer: a review." *Cancer Res* 60: 1777-88; Ralhan et al. 1998 "Circulating p53 antibodies as early markers of oral cancer: correlation with p53 alterations." *Clin Cancer Res* 4: 2147-52), shows, that p53 antibodies are associated with high grade tumors and poor survival. Several recent investigations have used the 2D proteomics approaches coupled with immunostaining with auto/heterologous sera to identify tumor antigens eliciting an immune response. Some of the antigens are β-tubulin, SM 22-α/CAI, annexin I and II, PGP9.5, RS/DJ I, MUC I, CK8, alpha enolase, aldehyde dehydrogenase, peroxiredoxin VI, and triose phosphate isomerase in different cancers and healthy individuals, (Le Naour. 2001 "Contribution of proteomics to tumor immunology." *Proteomics* 1: 1295-302; Prasannani et al. 2000 "Identification of beta-tubulin isoforms as tumor antigens in neuroblastoma." *Clin Cancer Res* 6: 3949-56; Brichory et al. 2001 "Proteomics-based identification of protein gene product 9.5 as a tumor antigen that induces a humoral immune response in lung cancer." *Cancer Res* 61: 7908-12; Klade et al. 2001 "Identification of tumor antigens in renal cell carcinoma by serological proteome analysis." *Proteomics* 1: 890-8; Brichory et al. 2001 "An immune response manifested by the common occurrence of annexins I and II autoantibodies and high circulating levels of IL-6 in lung cancer." *Proc Natl Acad Sci USA* 98: 9824-9; H. Yuichiro et al. 2003 "Circulating anti-MUC1 IgG antibodies as a favorable prognostic factor for pancreatic cancer." *Int. J Cancer* 103: 97-100; Gires et al. 2004 "Profile identification of disease-associated humoral antigens using AMIDA, a novel proteomics-based technology." *Cell Mol Life Sci* 61: 1198-207; Naour et al. 2002 "A distinct repertoire of autoantibodies in hepatocellular carcinoma identified by proteomic analysis." *Mol Cell Proteomics* 1: 197-203; Nakanishi et al. 2006 "Detection of eight antibodies in cancer patients' sera against proteins derived from the adenocarcinoma A549 cell line using proteomics-based analysis." *J Chromatogr B Analyt Technol Biomed Life Sci*; Li et al. 2006 "Proteomics-based identification of autoantibodies in the sera of healthy Chinese individuals from Beijing." *Proteomics* 6: 4781-9; Fujita et al. 2006 "Proteomics-based approach identifying autoantibody against peroxiredoxin VI as a novel serum marker in esophageal squamous cell carcinoma." *Clin Cancer Res* 12: 6415-20). However global autoantibody response has not been evaluated in cancers of gingivo-buccal complex. Identification of tumor antigens or their corresponding antibodies in serum have utility as indicators of risk for particular types of cancer or as diagnostic markers or as prognostic indicators.

It is becoming apparent that although some of the tumor antigens are expressed on the tumor cell surface, most of the tumor antigens identified so far are intracellular proteins (Yang and Yang. 2005 "New concepts in tumor antigens: Their significance in future immunotherapies for tumors." *Cellular and Molecular Immunology* 2: 331-341; Anderson and LaBaer. 2005 "The sentinel within: exploiting the immune system for cancer biomarkers." *J Proteome Res* 4: 1123-33). Some of the intracellular molecules such as cytokeratin 8 (Gires et al. 2005 "Cytokeratin 8 associates with the external leaflet of plasma membranes in tumour cells." *Biochem Biophys Res Commun* 328: 1154-62), enolase (Moscato et al. 2000 "Surface expression of a glycolytic enzyme, alpha-enolase, recognized by autoantibodies in connective tissue disorders." *Eur J Immunol* 30: 3575-84) and β actin (Wang et al. 2004 "Cell surface-dependent generation of angiostatin4.5." *Cancer Res* 64: 162-8) relocate to the cell membrane in cancer. In summary immune responses arise due to tumor specific alterations in protein expression, mutation, folding, degradation, intracellular localization (Anderson and LaBaer. 2005 "The sentinel within: exploiting the immune system for cancer biomarkers." *J Proteome Res* 4: 1123-33; Gires et al. 2005 "Cytokeratin 8 associates with the external leaflet of plasma membranes in tumour cells." *Biochem Biophys Res Commun* 328: 1154-62; Yang and Yang. 2005 "New concepts in tumor antigens: Their significance in future immunotherapies for tumors." *Cellular and Molecular Immunology* 2: 331-341) and their exposure to immune system following necrosis. Response to most tumor antigens is rarely observed in healthy individuals. Antibody immune responses therefore show promise as clinical biomarkers because antibodies have long half life in serum, are easy to measure and are relatively stable in blood samples' (Anderson and LaBaer. 2005 "The sentinel within: exploiting the immune system for cancer biomarkers." *J Proteome Res* 4: 1123-33; Gires et al. 2005 "Cytokeratin 8 associates with the external leaflet of plasma membranes in tumour cells." *Biochem Biophys Res Commun* 328: 1154-62; Robinson et al. 2002 "Autoantigen microarrays for multiplex characterization of autoantibody responses." *Nat Med* 8: 295-301; Yang and Yang. 2005 "New concepts in tumor antigens: Their significance in future immunotherapies for tumors." *Cellular and Molecular Immunology* 2: 331-341). Autoantigen microarray can be developed for multiplex characterization of autoantibody response. (Robinson et al. 2002 "Autoantigen microarrays for multiplex characterization of autoantibody responses." *Nat Med* 8: 295-301). It is reported in literature that no single marker is adequate for the detection and prognosis and several antigens would be required for high sensitivity and specificity (Yang and Yang. 2005 "New concepts in tumor antigens: Their significance in future immunotherapies for tumors." *Cellular and Molecular Immunology* 2: 331-341).

OBJECTS OF THE INVENTION

An object of the present invention is to provide identity of cellular protein antigens, which elicit autoantibody response in cancer of gingivo-buccal complex.

This invention identifies proteins, which elicit an antibody response in cancers of gingivo-buccal complex. It involves 2D proteomics approaches coupled with immunostaining with IgGs from sera of patients with cancer of gingivo-buccal complex and of healthy individuals and patients with leukoplakia. This is the first study for cancers of gingivo-buccal complex, which has evaluated presence of tumor antigens, which specifically elicit autoantibody response in patients.

Another object of the invention is to identify protein antigens as novel markers that are useful for screening, diagnostics and prognosis of the disease. Another object of the invention is to provide an array of proteins viz., three forms of alpha enolase, annexin HSP 70, peroxiredoxin VI, ATP synthase, alpha tubulin, beta tubulin, pyruvate kinase, triose phosphate isomerase, Phosphoglycerate mutase, aldose reductase, Cyclophilin A, which elicit autoantibody response in cancers of gingivo-buccal complex. None of these proteins have been reported earlier to elicit autoantibody response in cancers of gingivo-buccal complex and are therefore considered as new markers for cancers of gingivo-buccal complex.

SUMMARY OF THE INVENTION

Accordingly the present invention relates to identification of a set of proteins, which elicit an autoantibody response in patients with cancer of gingivo-buccal complex. Systematic comparisons of serum samples from clinically normal individuals and from patients with cancer of gingivo-buccal complex, and patients with leukoplakia, has revealed significant differences in the presence of autoantibodies in sera against cellular antigens present in an oral cancer cell line. The autoantibody response to a single or combination of these protein antigens serves as a novel marker and can be utilized for screening, early detection, prognosis, and potential target for therapy.

In an embodiment of the present invention Autoantibodies have been identified in sera against specific antigens which are useful as markers for cancer of gingivo buccal complex.

In an embodiment of the present invention Autoantibodies to antigens are selected from the group consisting of three forms of Alpha enolase, Annexin II, HSP 70, peroxiredoxin VI, ATP synthase, Pyruvate kinase, alpha tubulin, beta tubulin, Triose phosphate isomerase, Phosphoglycerate mutase, Aldose reductase and cyclophilin A.

In an embodiment of the present invention a method for detecting the cancer of gingivo-buccal complex comprising the following steps:—
a. contacting a serum sample derived from the subject suffering from the said cancer with one or more protein antigens selected from the group consisting of three forms of Alpha enolase, Annexin II, HSP 70, peroxiredoxin VI, ATP synthase, Pyruvate kinase, alpha tubulin, beta tubulin, Triose phosphate isomerase, Phosphoglycerate mutase, Aldose reductase and cyclophilin A, either individually or in any combination,
b. detecting immunospecific binding of the said protein antigens with the serum sample, In yet another embodiment of the present invention the immuno specific binding in patient suffering from cancer of gingivo-buccal complex is ranging from 50 to 100 percent higher than the control, In yet another embodiment of the present invention the binding is detected using an immunoassay, the said method comprising:
 i. immobilizing single or a combination of protein antigens onto a membrane or a support;
 ii. contacting the membrane or support obtained in step i) with the serum sample of the subject; and
 iii. detecting the presence of autoantibodies specific for a single or a combination of protein antigens bound to the substrate in the serum sample of the subject;
 iv. optionally, the binding is detected using multiplex protein array, comprising:—
  A. separating protein lysate from tumor cell line or tumor tissue lysate in several fractions or production of recombinant protein antigens;
  B. immobilizing different fractions or purified recombinant protein antigen obtained in step A) onto a membrane or a support harboring the protein array;
  C. contacting the membrane or support obtained in step B) with the serum sample of the subject;
  D. detecting the presence of autoantibodies specific for a single or a combination of protein antigens bound to the substrate in the serum sample of the subject using the multiplex protein array;

In yet another embodiment of the present invention the protein antigens are either naturally occurring or recombinant forms thereof.

In yet another embodiment of the present invention a kit for detecting the presence of cancer of gingivo-buccal complex comprising:
a) reagents capable of specifically detecting the presence or absence of autoantibodies specific for a single or a combination of protein antigens selected from the group consisting of three forms of Alpha enolase, Annexin II, HSP70, peroxiredoxin VI, ATP synthase, Pyruvate kinase, alpha tubulin, beta tubulin, Triose phosphate isomerase, Phosphoglycerate mutase, Aldose reductase and cyclophilin A;
b) instructions for using said kit for detecting the presence of cancer of gingivo-buccal complex in said human subject.

In yet another embodiment of the present invention the reagents in the kit comprising:—,
I. Recombinant protein or purified protein of identified tumor antigens in buffered saline containing chelating agents, protease inhibitor, reducing agent and non-ionic detergent.
II. Secondary antibody tagged with alkaline phosphatase or hoarse radish peroxidase, or FITC or Cy5.
III. Detection reagent such as BCIP/NBT or DAB or a fluorescent detector.
IV. Washing buffer as buffered saline containing non-ionic detergent.

In yet another embodiment of the present invention it provides use of the autoantibodies against proteins or recombinant forms of tumour antigens as markers for screening.

In yet another embodiment of the present invention it provides use of the kit for detection of cancer of gingivo-buccal complex in a subject.

In yet another embodiment of the present invention it provides use of the kit for prognosis of cancer of gingivo-buccal complex in a subject.

In yet another embodiment of the present invention use of the proteins or recombinant forms of tumour antigens selected from the group consisting of three forms of Alpha enolase, Annexin II, HSP 70, peroxiredoxin VI, ATP synthase, Pyruvate kinase, alpha tubulin, beta tubulin, Triose phosphate isomerase, Phosphoglycerate mutase, Aldose reductase and cyclophilin A as markers for screening of gingivo-buccal complex cancer.

The invention also provides for the use of the identified protein antigens in immunoassays designed to detect the presence of serum antibodies to the specific protein antigens in sera from individuals that harbor such antibodies.

The invention also relates to the use of the identified antigens as immunogens for stimulation of an immune response in patients expressing such protein antigens. The invention is demonstrated by way of example in which elevated levels of circulating antibodies reactive against tumor specific antigens were identified in sera derived from patients with cancer of gingivo-buccal complex.

It is believed that a new application of analyzing autoantibody response in patients with cancer of gingivo-buccal complex and clinically healthy individual (as an internal control) and patients with leukoplakia and comparing the profile of this response is a practical method for identifying clinically relevant tumor markers useful in risk stratification, detection, treatment monitoring, nodal status, detection of cancer recurrence and survival. The present invention is based on the detection of antibody response to a set of proteins, which indicates cancer of the gingivo-buccal complex in a patient. One or more of the identified markers or the pattern of markers can then be used in detection, prognosis, and/or treatment regimens related to cancer of the gingivo-buccal complex.

The present invention is related to diagnostic evaluation and prognosis of cancer by detecting autoantibodies to three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, and cyclophilin A in the serum of patients with cancer of gingivo-buccal complex. The detection of increased serum levels of autoantibodies to above-mentioned proteins constitute a novel strategy for screening, early detection and prognosis of cancers of gingivo-buccal complex.

The present invention provides for the use of three forms of Alpha enolase, Annexin peroxiredoxin VI, HSP 70, ATP synthase, Pyruvate kinase, alpha tubulin, beta tubulin, Triose phosphate isomerase, Phosphoglycerate mutase, Aldose reductase, and cyclophilin A protein antigens in immunoassay designed to detect the presence of serum antibodies to these protein antigens. Such immuoassay can be utilized for detection and prognosis of the cancer. In accordance with the invention measurement of antibody levels to three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A in a patient's serum can be used for the early detection of cancer. Moreover, the monitoring of serum antibody levels can be used to stage progression of the disease.

The invention further relates to the use of three forms of Alpha enolase, Annexin peroxiredoxin VI, HSP 70, ATP synthase, Pyruvate kinase, alpha tubulin, beta tubulin, Triose phosphate isomerase, Phosphoglycerate mutase, Aldose reductase, cyclophilin A proteins as antigens to immunize patients suffering from diseases characterized by increased antibody levels against these protein antigens. Stimulation of immunological response to such antigens is intended to elicit a more effective attack on tumor cells, which can thereby inhibit growth of tumor cells or facilitate the killing of tumor cells. The identification of autoantibodies to these protein antigens associated with cancers of gingivo-buccal complex provides a basis for immunotherapy of the disease.

The invention further provides for pre-packaged diagnostic kits, which can be conveniently used in clinical settings to diagnose patients having cancer or a predisposition to developing cancer. The kits can also be used to monitor the efficiency of agents used for treatment of cancer. In embodiment of invention, the kit comprises components for detecting and/or measuring the levels of autoantibodies directed towards three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A proteins in a sample.

The present invention is based on the increased levels of autoantibodies against three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A detected in the serum of the patients with cancer of gingivo-buccal complex. This finding provides a basis for development of diagnostic and prognostic methods as well as a means for monitoring the efficacy of various therapeutic treatments of cancer. The utility of identified antigens for early detection is assessed by analysis of sera from patients with leukoplakia of gingivo-buccal complex:

BRIEF DESCRIPTION OF THE DRAWINGS AND TABLES

FIG. 1 shows silver stained 2D gel of KB cell lysate with position of identified tumor antigens.

Figures 2A, 2B, 2C, 2D, 2E, 2F:
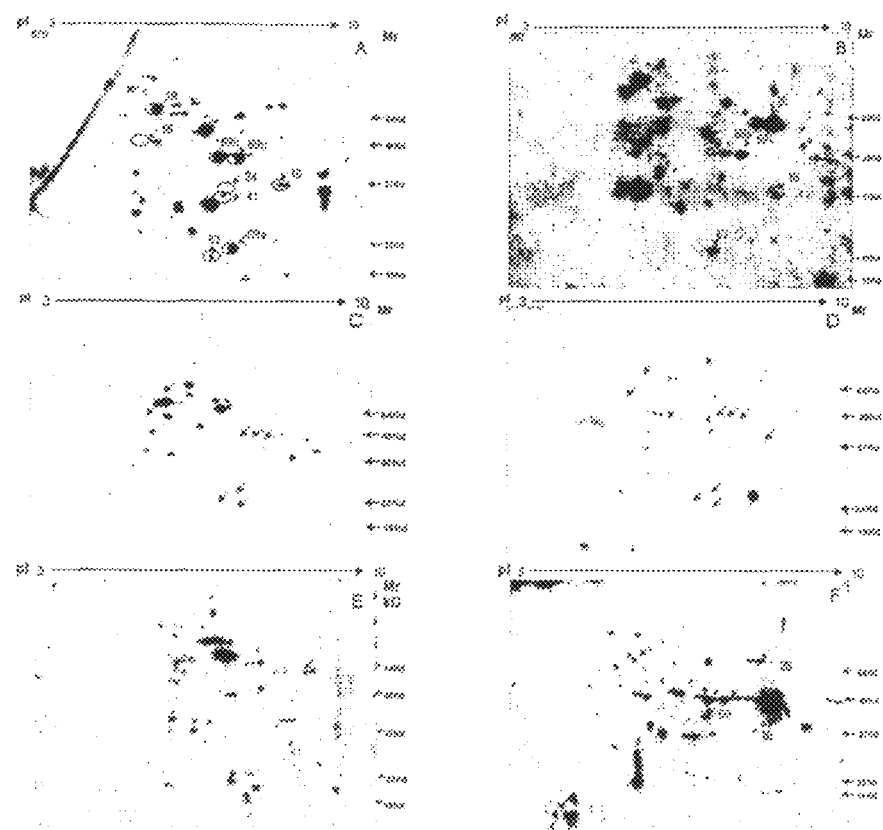
FIG. 2A and 2B show representative autographs of western blots of KB cell lysate separated by 2-D gel electrophoresis and probed with serum IgG from two patients with cancer of gingivo-buccal complex. Protein spots, which elicit an antibody response in several patients, are indicated by red arrows.
FIGS. 2C and 2D show representative autographs of western blots of KB cell lysate separated by 2-D gel electrophoresis and probed with serum IgG from two healthy individuals. Arrows show absence of immunoreactivity against protein spots, which are identified to elicit an antibody response in patients with cancer of gingivo-buccal complex.
FIGS. 2E and 2F show autographs of western blots of KB cell lysate separated by 2-D gel electrophoresis and probed with serum IgG from two patients with leukoplakia.

Table 1 Shows clinical data of the patients with cancer of gingivo-buccal complex from which sera was collected.

Table 2. Shows the auto antibody response in healthy individuals, patients with leukoplakia and cancer of gingivo-buccal complex.

Table 3 Shows the details of mass spectrometric analysis of the antigens eliciting an autoantibody response.

DETAILED DESCRIPTION OF THE INVENTION

The present invention achieves a highly desirable objective, namely the identification of novel cellular protein antigens for which individuals with cancers of gingivo-buccal complex carry autoantibodies in serum. Such protein antigens can in turn be purified and utilized to screen a patient's serum for the presence of circulating antibodies to such antigens, by means of sensitive and rapid immunoadsorbant assays or by other procedures. The invention also relates to using the novel protein antigens to immunize patients suffering from disease characterized by the increased levels of autoantibodies to such protein antigens. Stimulation of an immunological response to such antigens is intended to elicit a more effective attack on tumor cells which can thereby inhibit growth of tumor cells or facilitate the killing of tumor cells. The utility of the identified antigens for early detection is assessed by analysis of serum IgGs from patients with leukoplakia of gingivo-buccal complex.

Since cancer of the gingivo-buccal complex mainly arises due to alterations in several genes arising from exposure to tobacco products and exists in a precancerous state for a number of years, collection of serum from clinically normal healthy individual holds great diagnostic promise for the identification of early cancer markers. The co-expression pattern of these markers also provides the clinician a tool to assess response to therapy, recurrence, spread to nodes and survival of the patients.

Specifically, the method for identifying novel protein antigens, to which a patient with cancer of gingivo-buccal complex produces autoantibodies, comprises the following steps;
  a) extracting proteins from a sample of cells;
  b) separating the extracted proteins by two-dimensional electrophoresis;
  c) transferring the proteins separated by two-dimensional electrophoresis to a membrane;
  d) incubating the membrane with antiserum or IgGs purified from the serum of a patient known to have cancer of gingivo-buccal complex;
  e) detecting the proteins to which autoantibodies in the patients serum have bound; and
  f) comparing the proteins to which antibodies from the patient's serum sample bind, to the proteins to which antibodies from a control serum sample bind,
  g) wherein those proteins bound by antibodies in the patient's serum but not the control serum are identified by mass spectrometric analysis as proteins to which a patient with cancer of gingivo-buccal complex produces autoantibodies.

A wide variety of protein mixtures that contain antigens against which autoantibodies are present in serum can be prepared and separated into individual proteins by means of two-dimensional electrophoresis. Whole cell extracts can be analyzed for proteins, which have elicited autoantibodies. Alternatively, subsets of proteins such as secreted proteins, nuclear proteins or membrane proteins can be subjected to two-dimensional electrophoresis and analyzed separately for proteins which have elicited autoantibodies so as to increase the abundance of such proteins in the mixture.

The present invention aims to identify autoantibodies to multiple antigens without targeting particular antigen by means of two-dimensional electrophoretic separation followed by western blotting.

The present invention is based on the observation that serum from an individual that contains autoantibodies, such as a patient with cancer of gingivo-buccal complex, can be used to identify protein antigens expressed in cells of a particular tumor cell line or tumor tissue, to which the patient has autoantibodies. As described herein, serum from patients with cancer of gingivo-buccal complex contained antibodies which were immunospecific for three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A. The utility of the identified antigens for early detection is assessed by analysis of serum IgGs from patients with leukoplakia of gingivo-buccal complex.

Identification of Disease Associated Protein Antigens

The present invention provides a method for identifying cellular protein antigens to which patients with cancer of gingivo-buccal complex develop autoantibodies. The method is validated by the use of serum from individuals with cancer and from controls without cancer. A body fluid, which contains autoantibodies such as serum, is obtained from a patient known to have cancer of gingivo-buccal complex. A similar body fluid containing antibodies is obtained from a control subject that does not have cancer. Cells grown in cultures provide appropriate substitute for tumor tissue. Protein is extracted from cells in culture.

Two-dimensional gel electrophoresis is used to separate mixtures of proteins. Electrophoresis in the first dimension generally separates proteins based on charge, while electrophoresis in the second dimension referred to as SDS-PAGE, separates proteins based on size.

Prior to two-dimensional gel electrophoresis, aliquots of cells are solubilized using lysis buffer consisting of 8M urea, 2M thiourea, 2% CHAPS, 1% DTT in distilled deionized water.

Because isoelectrophoretic focusing is sensitive to charge modification, it is important to minimize protein alterations (e.g. proteolysis, deamidation of glutamine and asparagines, oxidation of cysteine to cystic acid, carbamylation) that can result from improper sample preparation. Thus, once solubilized, samples are stored frozen at −80° C.

Approximately 40 ug of protein is to be loaded on 7 cm individual gels. Prepared protein samples are loaded onto electrophoretic gels for isoelectric focusing separation in the first dimension, which separates proteins based on charge. Gel strips with immobilized gradient can be used for first dimension gel separation. After first dimension separation, proteins are transferred onto the second dimension gel, following an equilibration procedure and separated using SDS-PAGE, which separates proteins based on molecular weight. Multiple gels can be prepared for investigating sera from different patients. Method of two-dimensional gel electrophoresis are known to those skilled in the art. It can be done as previously described (Laemmli. 1970 "Cleavage of structural proteins during the assembly of the head of bacteriophage T4." *Nature* 227: 680-5). In most cases, aliquots are immediately applied onto isoelectric focusing gels (IEF). Generally isoelectric focusing is done at 250 V linearly for 20 min, 4000V linearly for 2 h, followed by exponential run of 10000 V/h. 12 gels can be run simultaneously. For the second dimension separation by SDS-PAGE, a 12% acrylamide gel can be used. If desired, protein spots in gels is visualized by the silver or commassie staining.

The second dimension separates proteins on the basis of molecular weight in a SDS gel. An 12% acrylamide gel provide effective separation of proteins having a mass range from 10000 to 180000 Da. Proteins outside this range are less well resolved. Proteins with molecular weight less than 10000 Da electrophorese close to the dye front and are less well resolved.

Following separation the proteins are transferred from the two-dimensional gels onto membranes commonly used for western blotting. The technique of western blotting and subsequent visualization of proteins are also known in the art (Towbin H. 1979 "Electrophoresis transfer of proteins from polyacrylamide gels to nitrocellulose sheets: procedure and some applications." *Proc Natl Acad Sci USA* 76: 4350-4354). The standard procedure is used. For immunoblotting IgG is purified from patient and control sera using the Melon Gel IgG Spin Purification Kit (45206) from Pierce Biotechnology. A second antibody specific for the first antibody is utilized in the procedure of western blotting analysis to visualize proteins that reacted with the first antibody.

It is expected that some proteins will be visualized as spots as a result of non specific reactivity with antibodies in the serum/IgG. Spots corresponding to proteins that have elicited specific antibodies are distinguishable from non specific spots on their presence in western blots prepared with patient's serum IgGs compared to control sera IgGs.

The protein spots, in two-dimensional gels of the same protein source used for western blots are visualized using a staining procedure. Spots in the gels that match the spots of interest on the autograph of western blots are identified by means of an overlay or a matching procedure between the gels and blots. Once the spots that contain proteins that have elicited autoantibodies are identified in two-dimensional gels, the protein can be extracted from the two-dimensional gels and identified by mass spectrometric analysis.

Alternatively western blots are stained with colloidal gold and the autographs are superimposed on the blots, to identify which spot on the autograph corresponds to which spot on the colloidal gold stained blot and in turn the silver stained gel.

Once a protein of interest has been identified, it is to be isolated and purified by standard methods, including chromatography (e.g., ion exchange, affinity, and sizing column chromatography), centrifugation, differential solubility, or by recombinant protein expression. Such purified proteins can be used in immunoassay designed to detect the presence of autoantibodies in a patient's serum, or such proteins preparations are to be used for immunization as described below.

The present invention is demonstrated by way of example wherein elevated levels of circulating autoantibodies reactive against three forms of Alpha enolase, Annexin peroxiredoxin VI, HSP 70, ATP synthase, Pyruvate kinase, alpha tubulin, beta tubulin, Triose phosphate isomerase, Phosphoglycerate mutase, Aldose reductase, cyclophilin A were detected in the sera of patients with cancer of gingivo-buccal complex. The utility of the identified antigens for early detection is assessed by analysis of serum IgGs from patients with leukoplakia of gingivo-buccal complex.

Immunoassay and Multiplex Protein Array

The present invention provides diagnostic and prognostic methods for cancers of gingivo-buccal complex based on detection of circulating autoantibodies against three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A in patients. The detection of autoantibodies in a sample from patient can be accomplished by any of a number of methods. Such methods include, but are not limited to competitive and non-competitive assay systems using techniques such as western blots, radioimmunoassays, ELISA (enzyme linked immunosorbant assay), sandwich immunoassay, immunoprecipitation, precipitin reactions, gel diffusion precipitin reactions, immunodiffusion assays, agglutination assays, complement fixation assays, immunoradiometric assays, fluorescent immunoassays, protein A immunoassays, to name but a few.

Such an immunoassay is carried out by a method comprising contacting a serum sample derived from a patient with a sample containing the protein antigen under condition such that specific antigen-antibody binding can occur, and detecting or measuring the amount of any immunospecific binding by the autoantibody. The levels of autoantibodies in a sample are compared to the levels present in an analogous sample from a portion of the body or from a subject not having the disorder.

The immunoassay can be conducted in a variety of ways. For example, one method to conduct such assays involves anchoring of three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A proteins onto a solid support and detecting corresponding autoantibodies specifically bound thereto. The protein antigen to be utilized in this assay of the invention can be prepared via recombinant DNA techniques well known in the art. For example DNA molecule encoding protein antigen or an antigenic fragment thereof can be genetically engineered into a appropriate expression vector for large scale preparation of antigenic protein. It is advantageous to engineer fusion proteins that can facilitate purification of protein antigen.

The present invention is demonstrated by way of example wherein elevated levels of circulating autoantibodies reactive against three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A have been detected in the sera of cancer patients. The detection of circulating autoantibodies in serum can be used in screening of subjects, who are at risk of cancer of gingivo-buccal complex, for prognostication and therapy.

Immunotherapy

The invention also relates to the use of three forms of Alpha enolase, Annexin peroxiredoxin VI, HSP 70, ATP synthase, Pyruvate kinase, alpha tubulin, beta tubulin, Triose phosphate isomerase, Phosphoglycerate mutase, Aldose reductase, cyclophilin A proteins as antigens to immunize patients suffering from cancers of gingivo-buccal complex. Stimulation of an immunological response to such antigens is intended to elicit a more effective attack on tumor cells which can thereby inhibit growth of tumor cells or facilitate the killing of tumor cells. The identification of autoantibodies to these protein antigens associated with cancers of gingivo-buccal complex provides a basis for immunotherapy of the disease.

The patient is immunized with the three forms of Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A protein antigens to elicit immune response which facilitates killing of tumor cells or inhibiting tumor cell growth. These proteins can be prepared using the methods described above for purification of proteins.

In an embodiment of the invention an immunogen comprising of three forms of purified Alpha enolase, Annexin II, peroxiredoxin VI, HSP 70, ATP synthase, Pyruvate kinase, alpha tubulin, beta tubulin, Triose phosphate isomerase, Phosphoglycerate mutase, Aldose reductase, cyclophilin A protein antigens (alone or in suitable combination) to which a patient with cancer of gingivo-buccal complex has developed autoantibodies, is used to elicit an immune response. For administration, these protein antigens should be formulated with a suitable adjuvant in order to enhance the immunological response to the protein antigen. Suitable adjuvant include, but are not limited to mineral gels, e.g. aluminium hydroxide, surface active substances such as lysolecithin, pluronic polyols, polyanions, peptides, oil emulsions, and potentially useful human adjuvant such as BCG (bacilli Calmett-Guerin) and *Corynebacterium parvum*. Many methods are used to introduce the formulations derived above; including but not limited to oral, intradermal, intramuscular, intraperitoneal, intravenous, and subcutaneous.

EXAMPLES

The following examples are given by way of illustration of the present invention and therefore should not be construed to limit the scope of the present invention.

Example 1

Patients

Patients who received no prior therapy and presented to the Tata Memorial Hospital, Parel, Mumbai were eligible to participate in this institutional review board-approved prospective investigation if they had biopsy-proven unilateral primary invasive cancer of gingivo-buccal complex and gave written consent to undergo blood collection. To determine whether autoantibody pattern in patients with cancer of gingivo-buccal complex was similar to or different from those in healthy individuals and patients with leukoplakia, blood was collected from patients with cancer, leukoplakia and healthy individuals. Sera were obtained from the blood and the IgGs were purified from sera of patients and healthy individuals using Melon Gel IgG Spin Purification Kit (45206) from Pierce Biotechnology. Clinical information of the patients with cancer of gingivo-buccal complex is given in Table 1.

| | Clinical information of the patients with cancer of the gingivo buccal complex | | | | |
|---|---|---|---|---|---|
| S. No. | Sample number | Age | Sex | TNM staging | Differentiation status |
| 1 | 82 | 68 | F | — | MD |
| 2 | 660 | 37 | M | T1N0M0 | MD |
| 3 | 493 | 29 | F | T2N0M0 | MD |
| 4 | 697 | 56 | M | T2N1M0 | WD |
| 5 | 190 | 55 | F | T2N1M0 | SQ C |
| 6 | 666 | 38 | M | T2N2CM0 | MD |
| 7 | 825 | 40 | F | T2N2M0 | MD |
| 8 | 623 | 51 | M | T3N0M0 | WD |
| 9 | 495 | 43 | M | T3N0M0 | SSC |
| 10 | 417 | 35 | M | T3N0M0 | PD |
| 11 | 902 | 60 | F | T3/4N0M0 | WD |
| 12 | 420 | 46 | M | T3/4N0M0 | MD |
| 13 | 451 | 35 | M | T3/4N1M0 | WD |
| 14 | 365 | 50 | F | T3/4N2aM0 | PD |
| 15 | 883 | 65 | F | T4N0M0 | MD |
| 16 | 756 | 60 | F | T4N0M0 | MD |
| 17 | 766 | 50 | F | T4N0M0 | MD |
| 18 | 136 | 49 | F | T4N0 | SQ C |
| 19 | 358 | 65 | M | T4N0M0 | WD |
| 20 | 460 | 52 | M | T4N0M0 | PD |
| 21 | 356 | 43 | M | T4N1M0 | PD |
| 22 | 792 | 40 | M | T4N1M0 | WD |
| 23 | 828 | 60 | F | T4N1M0 | PD |
| 24 | 867 | 56 | M | T4N1M0 | PD |
| 25 | 423 | 58 | F | T4N1M0 | MD |
| 26 | 922 | 55 | M | T4N1M0 | PD |

-continued

Clinical information of the patients with cancer of the gingivo buccal complex

| S. No. | Sample number | Age | Sex | TNM staging | Differentiation status |
|---|---|---|---|---|---|
| 27 | 925 | 55 | F | T4N1M0 | PD |
| 28 | 670 | 80 | F | T4N2M0 | MD |

Example 2

Specimen Preparation, Two-Dimensional Polyacrylamide Gel Electrophoresis, Western Blotting and Mass Spectrometry Analysis The human cancer cell line, KB was used in this study. KB cells were grown in DMEM (Gibco) supplemented with 10% Fetal bovine serum (JRH Biosciences), streptomycin (1 g/lit), gentamicin (80 mg/lit), Amphotericin B (2.5 mg/lit). Cells were harvested and washed with phosphate-buffered saline (PBS), and cells were lysed using buffer consisting of 8 M urea, 2M Thiourea, 2% CHAPS, 1% DTT. The sample was kept at room temperature for 30 min and ultracentrifuged at 55000 rpm at 4° C. for 1 h. The supernatant was collected in microtube. The lysate was aliquoted and stored at −80° C. until use. Quantitation of protein was done by modified Lowry method (Peterson. 1977 "A simplification of the protein assay method of Lowry, et al which is more generally applicable." *Anal Biochem* 83: 346-356). An aliquot of 40 ug of protein was loaded onto a 7-cm IEF strip, pH 3 to 10. Focusing was conducted on IEF cells at 250 V for 20 minutes followed by a linear increase to 4000 V for 2 hours. The focusing was terminated by logarithmic increase at 10,000 volt-hours. Strips were then equilibrated in 375 mM Tris buffer, pH 8.8, containing 6M urea, 20% glycerol, 2% DTT, and 2% sodium dodecyl sulfate. Fifteen minutes later, buffer is discarded and strips were equilibrated in separate buffer containing 375 mM Tris buffer, pH 8.8, containing 6M urea, 20% glycerol, 2.5% idoacetamide, and 2% sodium dodecyl sulfate. Fifteen minutes after the addition of iodoacetomide containing buffer, strips were dipped in running buffer containing 20 mM Tris, 190 mM glycine and 0.2% SDS. Strips were then loaded onto the second dimension using mini protean 3 dodeca cell (Bio-Rad) with 12% acrylamide gel. Gels were then transferred to PVDF membranes. One gel was stained by using Silver or commassie brilliant blue R 250 (sigma) dye. After transfer, membrane/2D blots were blocked with 5% non-fat milk powder in 20 mM Tris (pH 7.5) buffer saline with 0.1% tween 20 (TBST) for 1 h. After blocking, 2D blots were incubated separately with serum IgGs from patient with cancers of gingivo-buccal complex, and from healthy individuals, and patients with leukoplakia, at dilution of 5 ug/ml for overnight, followed by washing with TBST and incubation with HRP conjugated Anti human IgG as a secondary antibody for 1 h. After secondary antibody incubation, signal detection was done by enhanced chemiluminescence (Amersham Biosciences) followed by autoradiography on X-ray film (Kodak). After immunodetection, the membranes were stripped with destainer (40% methanol and 10% acetic acid) washed with TBST and stained with Colloidal Gold (BioRad) to obtain the pattern of the separated proteins. Autograph patterns on the X-ray film were overlayed on the Colloidal gold stained blots to identify proteins, which react with the IgGs from cancer sera or control IgGs and their patterns were then matched to the silver stained gel run simultaneously. This was further confirmed with the assistance of Microsoft PhotoDraw V2 software. Protein spots of interest were excised from the silver stained/commassie stained gel and were destained with 100 µl of destaining solution (30 mM potassium ferricyanide/100 mM sodium thiosulfate mixed 1:1 v/v). After thorough rinsing with water, the gel was dehydrated in 100% ACN and lyophillised. The proteins in the plugs were trypsinized overnight with 10 ng/µl of trypsin (Sigma) in 25 mM ammonium bicarbonate in water and the peptides were recovered by extraction with 50% ACN/5% TFA. The peptide mixture was subjected to mass spectrometry on the Applied Biosystems 4800 MALDI-TOF-TOF instrument. The identity of the protein was obtained by analysis of the peak list using the MASCOT search engine.

Gel Image Analysis

Gel images were captured using PDQuest software (Bio-Rad).

KB cell proteins were separated by 2-D PAGE and transferred onto Immobilon-PVDF membranes. For western blot analysis, each membrane was treated with one serum IgG sample. The samples included sera IgGs obtained at the time of diagnosis from 28 patients with cancer of gingivo-buccal complex (Table 1), and from 16 healthy individuals, and 12 patients with leukoplakia.

An example of a 2-D gel of KB cells stained with silver is shown in FIG. 11*t* also represents the pattern on the PVDF membranes after transfer.

Hybridization of membranes using patient's sera IgGs as the primary antibody and sheep anti human IgGs as a secondary antibody revealed variable patterns of reactivity among patient sera IgGs with cancer of gingivo-buccal complex, (FIGS. 2A and 2B). In general, several reactive spots were observed with most sera. Some of the reactive spots were observed with control sera and thus were considered to represent non-specific reactivity. Others were restricted to sera IgG of patient with cancer of gingivo-buccal complex. Most noticeable reactivity was observed for three forms of alpha enolase (spot 59*a*, *b* and *c*), which were detected by 50%, 79%, 75% patients with cancer of gingivo-buccal complex. Other protein antigen, which were detected by sera IgGs of patients with cancer of gingivo-buccal complex were Annexin II (50%), peroxiredoxin VI (54%), HSP 70 (43%), ATP synthase (25%), Pyruvate kinase (32%), alpha tubulin (29%), beta tubulin (29%), phosphoglycerate mutase (25%), Triose phosphate isomerase (14%), Aldose reductase (18%), cyclophilin A (7%).

To ensure specificity of autoantibodies, which were detected in sera of patients with cancer of gingivo-buccal complex, 2-D blots of KB cell lysate proteins were also immunostained with IgGs purified from sex matched healthy individuals in the same age group. FIGS. 2C and 2D shows the pattern of autograph signals obtained with serum IgG from two healthy individuals. Sera of healthy individuals had autoantibodies against alpha enolase, 59*a*, 59*b*, and 59*c* in 12.5%, 19%, and 37.5% respectively. Autoantibodies against aldose reductase and pyruvate kinase were seen only in one of sixteen healthy individuals.

The utility of identified antigens for early detection was assessed by analysis of sera from patients with leukoplakia of gingivo-buccal complex. FIGS. 2E and 2F show representative profiles of the autograph signals obtained by immunostaining of 2D blots of KB cell lysate with serum IgG of patients with leukoplakia of gingivo-buccal complex. Some of the spots, which were detected by IgGs purified from sera of patients with cancer of the gingivo buccal complex, were also detected by IgGs purified from sera of patients with leukoplakia Table 2, shows the percentage occurrence of each of the spots in healthy individuals, patients with cancer of gingivo-buccal complex and leukoplakia. The identity of the proteins obtained by mass spectrometric analysis is given in Table 3.

TABLE 2

Auto antibody response in healthy individuals, patients with leukoplakia and cancer of gingivo-buccal complex.

| | | % Occurrence | | |
|---|---|---|---|---|
| Spot | Protein identity | Healthy individuals | Leukoplakia | GBC Cancer |
| 59b | Alpha enolase | 19 | 17 | 79 |
| 59c | Alpha enolase | 37.5 | 75 | 75 |
| 59a | Alpha enolase | 12.5 | 25 | 50 |
| 16 | Annexin II | — | 25 | 50 |
| 52 | Peroxiredoxin VI | — | 8 | 54 |
| 19 | HSP 70 | — | 17 | 43 |
| 26 | Pyruvate kinase | 6 | 25 | 32 |
| 15 | Alpha tubulin | — | 8 | 29 |
| 10 | Beta tubulin | — | 17 | 29 |
| 65 | ATP synthase | — | 8 | 25 |
| 69a | Phosphoglycerate mutase | — | 8 | 25 |
| 41 | Aldose reductase | 6 | 17 | 18 |
| 69b | Triose phosphate isomerase | — | 8 | 14 |
| 70b | Cyclophilin A | — | — | 7 |

TABLE 3

Mass Spectrometric analysis of antigens eliciting an autoantibody response

| | | | | MS analysis | | | | MS/MS |
|---|---|---|---|---|---|---|---|---|
| Spot | ID | Accession number | Theoretical Mr/pI | Observed Mr/pI | Score | Sequence coverage | Peptide matched | analysis Score |
| 59a | Alpha enolase | P06733 | 47.3/6.99 | 50/6.8 | 198 | 54 | 17/33 | |
| 59b | Alpha enolase | P06733 | 47.3/6.99 | 50/7.1 | 175 | 58 | 19/50 | 233 |
| 59c | Alpha enolase | P06733 | 47.3/6.99 | 50/7.4 | 274 | 65 | 21/35 | 602 |
| 52 | Peroxiredoxin VI | P30041 | 25/6 | 25/7 | 150 | 56 | 11/32 | 305 |
| 19 | HSP 70 | P08107 | 70.2/7 | 70/6.5 | 257 | 48 | 20/50 | 320 |
| 16 | Annexin II | P07355 | 38.6/7.5 | 37/8 | 247 | 65 | 22/50 | 249 |
| 69a | Phosphoglycrate mutase 1 | P18669 | 28.7/6.75 | 26/7.3 | 263 | 65 | 24/50 | 211 |
| 69b | Triose phosphate isomerase | P60174 | 26.8/6.51 | 25/7.3 | 249 | 77 | 18/47 | 325 |
| 10 | Beta tubulin | P07437 | 50/4.78 | 50/5.3 | 290 | 56 | 29/37 | 182 |
| 15 | Alpha tubulin | P68363 | 50.8/4.94 | 50/5.5 | 281 | 59 | 21/35 | 716 |
| 65 | ATP synthase | P06576 | 56.5/5.26 | 55/5.5 | 119 | 21 | 8/8 | 130 |
| 26a | Pyruvate kinase m1/m2 | P14618 | 58.3/7.95 | 55/8 | 182 | 49 | 23/50 | 161 |
| 26b | Pyruvate kinase m1/m2 | P14618 | 58.3/7.95 | 55/8.2 | 345 | 58 | 25/35 | 312 |
| 41 | Aldose reductase | P15121 | 36/6.56 | 35/7 | 159 | 47 | 15/35 | 110 |
| 70b | Cyclophilin A | P62937 | 18.1/7.82 | 14/8 | 109 | 75 | 10/30 | 273 |

ADVANTAGES OF THE INVENTION

1. Systematic comparisons of serum samples from clinically normal individuals and from patients with cancer of gingivo-buccal complex has revealed significant differences in the presence of autoantibodies against several antigens present in an oral cancer cell line.

2. These autoantibodies markers can be useful for screening, detection, prognosis, and therapy of gingivo-buccal cancer, with high efficiency.

3. These autoantibody markers are easy to screen or measure using immunoassay and other detection methods.

4. This is the first study for cancers of gingivo-buccal complex, which has evaluated presence of tumor antigens, which specifically elicit autoantibody response in patients.

We claim:

1. A method for treating a subject with cancer of gingivo-buccal complex comprising detecting the presence in serum taken from said subject of autoantibodies specific for a combination of protein antigens comprising three forms of Alpha enolase, Annexin II, and peroxiredoxin VI, in an amount greater than that found in healthy subjects and thereafter administering to said subject an immunotherapeutic amount of at least one of said protein antigens by oral, intradermal, intramuscular, intraperitoneal or subcutaneous means.

2. A method as claimed in claim 1 wherein the subject is a mammal.

3. A method as claimed in claim 1, wherein said detection is effected by contacting serum from the subject with a reagent comprising:
   I. The combination of protein antigens as specified in claim 1, wherein said protein antigens are recombinant or purified, in buffered saline containing chelating agents, protease inhibitor, reducing agent and non-ionic detergent;
   II. Secondary antibody tagged with alkaline phosphatase or horseradish peroxidase, or FITC or Cy5; and
   III. Detection reagent.

4. A method as claimed in claim 3, wherein the subject is a mammal.

5. The method as claimed in claim 3, wherein the detection reagent is BCIP/NBT, DAB or a fluorescent detector.

6. The method as claimed in claim 1 wherein said detection further includes detection of autoantibodies to at least one of HSP70, ATP synthase, Pyruvate kinase, alpha tubulin, beta tubulin, Triose phosphate isomerase, Phosphoglycerate mutase, Aldose reductase and cyclophilin A in said serum in an amount greater than that found in healthy subjects.

7. A method for treating cancer of gingivo-buccal complex which comprises carrying out an immunotherapy to a subject who has been determined to suffer from such cancer by detecting the presence in serum taken from said subject of autoantibodies specific for a combination of protein antigens comprising three forms of Alpha enolase, Annexin II, and peroxiredoxin VI, in an amount greater than that found in healthy subjects wherein said immunotherapy comprises administering to said subject an immunotherapeutic amount of at least one of said protein antigens by oral, intradermal, intramuscular, intraperitoneal or subcutaneous means.

8. A method as claimed in claim 7, wherein said detection is effected by contacting serum from the subject with a reagent comprising
   I. The combination of protein antigens as specified in claim 7, wherein said protein antigens are recombinant or purified, in buffered saline containing chelating agents, protease inhibitor, reducing agent and non-ionic detergent;
   II. Secondary antibody tagged with alkaline phosphatase or horseradish peroxidase, or FITC or Cy5; and
   III. Detection reagent.

9. The method as claimed in claim 8, wherein the detection reagent is BCIP/NBT, DAB or a fluorescent detector.

10. the method as claimed in claim 7 wherein said detection further includes detection of autoantibodies to at least one of HSP70, ATP synthase, Pyruvate kinase, alpha tubulin, beta tubulin, Triose phosphate isomerase, Phosphoglycerate mutase, Aldose reductase and cyclophilin A in said serum in an amount greater than that found in healthy subjects.

* * * * *